United States Patent [19]

Ward

[11] Patent Number: 4,473,572

[45] Date of Patent: Sep. 25, 1984

[54] $\alpha_2$-ADRENOCEPTOR ANTAGONISTIC BENZOQUINOLIZINES

[75] Inventor: Terence J. Ward, Slough, England

[73] Assignee: John Wyeth & Brother, Limited, Maidenhead, England

[21] Appl. No.: 471,911

[22] Filed: Mar. 3, 1983

[30] Foreign Application Priority Data

Mar. 18, 1982 [GB] United Kingdom ............... 8207943

[51] Int. Cl.³ .................... A61K 31/47; C07D 455/06
[52] U.S. Cl. ...................................... 424/258; 546/95
[58] Field of Search .......................... 546/95; 424/258

[56] References Cited

U.S. PATENT DOCUMENTS 4,076,820 2/1978 Archibald et al. ................. 424/258

FOREIGN PATENT DOCUMENTS 2083029 9/1983 United Kingdom ................. 546/95

Primary Examiner—Richard A. Schwartz
Attorney, Agent, or Firm—George Tarnowski

[57] ABSTRACT

The invention concerns benzoquinolizines of formula

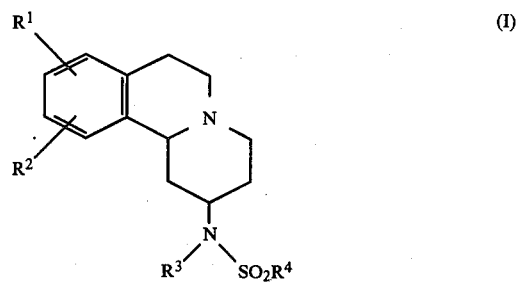

and their pharmaceutically acceptable acid addition salts. In the formula, $R^1$ and $R^2$ which may be the same or different, each represent hydrogen, lower alkyl, lower alkoxy or halogen, $R^3$ represents methyl or ethyl and $R^4$ represents halo(lower)alkyl. The compounds possess $\alpha_2$-adrenoceptor antagonistic activity and can be incorporated into pharmaceutical compositions.

7 Claims, No Drawings

$\alpha_2$-ADRENOCEPTOR ANTAGONISTIC BENZOQUINOLIZINES

This invention relates to benzoquinolizines, to processes for preparing the benzoquinolizines, to their use and to pharmaceutical compositions containing them.

The novel compounds of the invention are benzoquinolizines of the general formula (I)

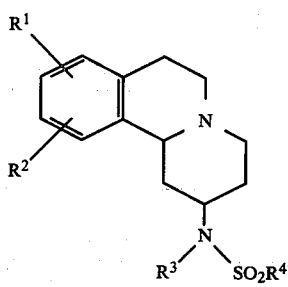
(I)

and their pharmaceutically acceptable acid addition salts. In formula (I), $R^1$ and $R^2$ which may be the same or different, each represent hydrogen, lower alkyl, lower alkoxy or halogen, $R^3$ represents methyl or ethyl and $R^4$ represents halo(lower)alkyl.

The term "lower" as used herein means that the radical referred to contains 1 to 6 carbon atoms. Preferably such radicals contain 1 to 4 carbon atoms. For example a lower alkyl group may be methyl, ethyl, propyl or butyl. When $R^1$ and/or $R^2$ represent lower alkoxy the group may be, for example, methoxy, ethoxy, propoxy or butoxy. When $R^1$ and/or $R^2$ represents halogen the substituent may be, for example, fluorine, chlorine or bromine. Preferably both $R^1$ and $R^2$ are hydrogen.

$R^3$ is preferably methyl.

The halo substituent in the $R^4$halo(lower)alkyl group may be fluorine, chlorine, bromine or iodine. More than one halo atom may be present in the halo(lower)alkyl group; if more than one halo atom is present the halo atoms may be on the same carbon atom of the (lower)alkyl radical or on different carbon atoms if the (lower) radical contains more than one carbon atom. Examples of halo(lower)alkyl groups include, for example, trifluoromethyl; chloromethyl; 2,2,2-trifluoroethyl and 3-chloropropyl.

The compounds of the present invention may be prepared by reacting a reactive derivative of a sulphonic acid of the formula (II)

$R^4SO_2OH$ (II)

(where $R^4$ is as defined above) with a 2-methylamino- or 2-ethylamino-benzoquinolizine of the general formula (III)

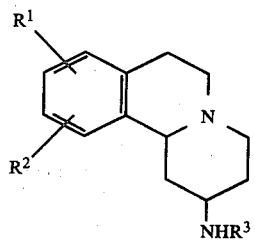
(III)

where $R^1$, $R^2$ and $R^3$ have the meanings given above, and if required, converting a free base into a pharmaceutically acceptable acid addition salt. The reactive derivative of the sulphonic acid can be, for example, the acid halide or anhydride. Preferably it is the halide i.e. a compound of formula $R^4SO_2X$ (wherein $R^4$ is as defined above and X is halogen, preferably chlorine). The reaction is conveniently carried out under basic conditions, for example in the presence of a tertiary amine, e.g. triethylamine. If $R^4$ is 2-haloethyl the amine of formula III is preferably reacted with the sulphonic acid anhydride under neutral conditions to prevent elimination of hydrogen halides from the product. The starting compound of formula (III) may be prepared, for example, by the methods disclosed in U.K. Specification No. 1,513,824.

In an alternative method of preparing the compounds of the invention a benzoquinolizine alcohol of general formula (IV)

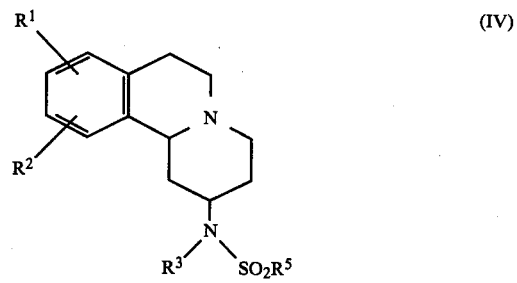
(IV)

wherein $R^1$, $R^2$ and $R^3$ have the meanings given above and $R^5$ is hydroxy(lower)alkyl may be reacted with a hydroxyl/halogen exchange reagent. By the term "hydroxyl/halogen exchange reagent" is meant a reagent capable of displacing the hydroxyl group of an alcohol by a halogen atom. Typical examples are phosphorus trichloride, and pentachloride and thionyl chloride. The starting alcohol of formula (IV) may be prepared from the amine of formula (III) by, for example, reacting the amine with an alkoxy or benzyloxy-alkane-sulphonic anhydride or acid chloride and then removing the alkyl or benzyl protecting group from the hydroxy radical.

In another method of preparing the compounds of the invention a hydrogen halide (e.g. hydrogen chloride) or a halogen (e.g. chlorine) is added across the double bond of a benzoquinolizine of formula (V)

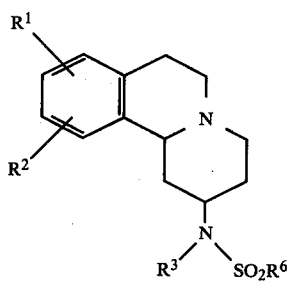
(V)

wherein $R^1$, $R^2$ and $R^3$ have the meanings given above and $R^6$ is a (lower) alkenyl group. The benzoquinolizines of formula (V) may be prepared by, for example, condensing a reactive derivative of an alkenesulphonic acid (e.g. the sulphonyl chloride) with an amine of general formula (III).

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence can exist in various stereochemical forms. In addition they can exist as cis or trans isomers. It will be realised that if the starting material of formula (III) is a mixture of isomers the product of formula (I) will also be a mixture of isomers, unless the mixture is separated by standard procedure. The preferred compounds of the invention are the trans isomers in which the $-NR^3SO_2R^4$ group is in the equatorial position i.e. compounds of the general formula (VI)

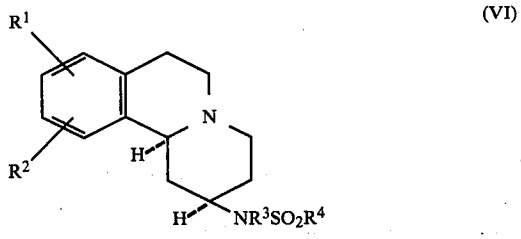

(VI)

and the pharmaceutically acceptable acid addition salts thereof. These compounds can be prepared by the methods described from the corresponding trans isomer starting material.

The compounds of the present invention possess pharmacological activity. In particular the compounds possess $\alpha_2$-adrenoceptor antagonistic activity in warm blooded animals and hence are of value in conditions where antagonism of the $\alpha_2$-adrenoceptor is desirable, for example as antidepressants, in treatment of diabetes and in inhibiting blood platelet aggregation.

The compounds of the invention were tested for their $\alpha_2$-adrenoceptor antagonistic activity on the rat field stimulated vas deferens preparation using a modification of the method of Drew, Eur.J.Pharmac., 1977, 42, 123-130. The procedure is described below.

Desheathed vas deferentia from sexually mature rats were suspended in a 6 ml organ bath in Krebs solution at 37° and bubbled with 5% $CO_2$ in oxygen. Platinum ring electrodes were positioned above and below the tissue for field stimulation, the stimulus parameters being 0.1 Hz 1 ms pulse width at supramaximal voltage. Twitch responses were recorded isotonically with a 0.5 g loading. Clonidine hydrochloride was used as the $\alpha$-adrenoceptor agonist and cumulative concentration-response curves were constructed for the inhibition of twitch obtained with clonidine in the range 0.125 to 4 ng $ml^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producing 50% inhibition of twitch before and after introduction of antagonist were obtained and the dose-ratio for clonidine was calculated. Various concentrations of the antagonists were used.

These results were plotted in the manner described by Arunlakshana & Schild, Br.J.Pharmac. Chemother., 1959, 14, 48-58 and the values of $pA_2$ and slope were calculated. The compounds of the invention possess potent $\alpha_2$-adrenoceptor antagonistic activity. The results are shown in the following Table I:

TABLE I

| Compound of Example | $pA_2$ ($\alpha_2$) |
|---|---|
| 1 | 7.15 |
| 2 | 7.56 |
| 3 | 8.05 |
| 4 | 8.08 |

The compounds of the invention have been found to antagonise the $\alpha_2$-adrenoceptors to a much greater extent than the $\alpha_1$-adrenoceptors. The $\alpha_1$ antagonistic activity can be evaluated by a number of different methods. One method involves assessing the activity on the isolated anococcygeus muscle of the rat. The method is based on that of Gillespie, Br.J.Pharmac., 1972, 45, 404-416. In the procedure male rats (250-360 g) are killed by a blow on the head and bled. The two anococcygeus muscles are removed from their position in the midline of the pelvic cavity, where they arise from the upper coccygeal vertebrae. The muscles are suspended in 5 ml organ baths in Krebs solution containing $10^{-4}M$ ascorbic acid, to prevent drug oxidation. The tissues are gassed with a 95% oxygen, 5% $CO_2$ mixture and maintained at 37°. Longitudinal muscle contractions are recorded using isotonic transducers. Cumulative dose response curves are then obtained to phenylephrine or in some cases methoxamine, both agents being presynaptic alpha adrenoceptor agonists. The concentration range of phenylephrine or methoxamine used is 0.02 to 0.8 $\mu g.ml^{-1}$. The agonist is then washed from the bath and the test drug added to the bathing medium at a concentration of $10^{-6}M$. After 30 min. equilibration with the test drug a further agonist dose response curve is obtained. The washing, equilibration and agonists dosing procedures are then repeated using $10^{-5}M$ and $10^{-4}M$ solutions of the test drug. Estimates of the $pA_2$ value for the test drug as an antagonist of phenylephrine or methoxamine were made from the agonist dose-ratios using the method of Arunlakshana & Schild, Br.J.Pharmac.Chemother., 1959, 14, 48-58.

The $pA_2$ for $\alpha_1$ antagonistic activity and the $\alpha_2/\alpha_1$ selectivity for compounds of the invention are given in Table II below.

TABLE II

| Compound of Example | $pA_2$ ($\alpha_1$) | $\alpha_2/\alpha_1$ selectivity* |
|---|---|---|
| 1 | 5.49 | 46 |
| 2 | 5.93 | 43 |
| 3 | 6.61 | 45 |
| 4 | 6.54 | 27.5 |

*antilog of ($\alpha_2pA_2 - \alpha_1pA_2$)

The invention further provides a compound of formula (I) or a pharmaceutically acceptable acid addition salt for use in antagonising $\alpha_2$-adrenoceptors in a mammal.

The invention also provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxylmethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceuitcal compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg or less to 750 mg or more; according to the particular need and the activity of the active ingredient. The invention also includes the compounds in the absence of the carrier where the compounds are in unit dosage form.

The following Examples illustrate the invention:

EXAMPLE 1

N-Methyl-N-(1,3,4,6,7,11bα-hexahydro-2H-benzo[a]-quinolizin-2β-yl)-trifluoromethanesulphonamide A solution of 2β-methylamino-1,3,4,6,7,11bα-hexahydro-2H-benzo[a]quinolizine (2.16 g) and triethylamine (1.15 g) in dichloromethane (25 cm$^3$) was cooled to $-20°$ and stirred as a solution of trifluoromethanesulphonic anhydride (2.82 g) in dichloromethane (25 cm$^3$) was added slowly. The mixture was stirred at $-20°$ for 0.5 h, then allowed to stand overnight at room temperature, and then for a further 24 h. The mixture was washed with water (2×25 cm$^3$), dried (MgSO$_4$), filtered and evaporated to give a red-brown syrup (3.02 g). This was chromatographed on silica eluted with an increasing percentage of ethanol in ethyl acetate. The main product (0.72 g) was separated from starting material at the 10% ethanol/ethyl acetate level, dissolved in ethanol, acidified with ethanolic HCl, diluted with ethyl acetate and cooled. Two crops of the title compound hydrochloride (0.58 g) were obtained as off-white, feathery crystals, m.p. 220°–225° (dec.).

EXAMPLE 2

N-Methyl-N-(1,3,4,6,7,11bα-hexahydro-2H-benzo[a]-quinolizin-2β-yl)-2′,2′,2′-trifluoroethanesulphonamide An ice-cold, stirred solution of 2β-methylamino-1,3,4,6,7,11bα-hexahydro-2H-benzo[a]quinolizine (2.16 g) and triethylamine (1.2 g) in dichloromethane (25 cm$^3$) was treated slowly with a solution of 2,2,2,-trifluoroethanesulphonyl chloride (1 cm$^3$ 1.654 g) in dichloromethane (25 cm$^3$). The clear solution was kept at room temperature for 5 days, washed with water (2×50 cm$^3$), dried (MgSO$_4$), filtered and evaporated to a syrup which was chromatographed on silica eluted with 10% ethanol-ethyl acetate to give a yellow syrup (2.88 g). This was dissolved in hot ethanol (10 cm$^3$), acidified with ethanolic HCl, diluted with ethyl acetate (25 cm$^3$) and allowed to crystallise over several days. The crystals were filtered, washed with 10% ethanol-ethyl acetate, then triturated with boiling ethanol (15 cm$^3$). After cooling, filtration gave pure title compound as the hydrochloride, colourless crystals, m.p. 227°–230° (dec).

EXAMPLE 3

N-Methyl-N-(1,3,4,6,7,11bα-hexahydro-2H-benzo[a]-quinolizin-2β-yl)chloromethanesulphonamide An ice-cold, stirred solution of 2β-methylamine-1,3,4,6,7,11bα-hexahydro-2H-benzo[a]quinolizine (2.16 g) and triethylamine (1.2 g) in dichloromethane (25 cm$^3$) was slowly treated with a solution of chloromethanesulphonyl chloride (1.49 g) in dichloromethane (25 cm$^3$). The clear solution was kept at room temperature for 3 days, then washed with water (25 cm$^3$), brine (25 cm³), and dried (MgSO₄). Filtration and evaporation gave a red-orange gum which was chromatographed on silica eluted with 10% ethanol-ethyl acetate to give a yellow gum (2.13 g). This was dissolved in ethanol (5 cm³), acidified with ethanolic HCl, diluted with ethyl acetate (25 cm³) and cooled. Crystals slowly formed. These were collected by filtration to give the title compound as the hydrochloride, colourless crystals, m.p. 225°–230° (dec; softens above 220°).

EXAMPLE 4

N-Methyl-N-(1,3,4,6,8,11bα-hexahydro-2H-benzo[a]quinolizin-2β-yl)-3′-chloropropanesulphonamide An ice-cold, stirred solution of 2β-methylamino-1,3,4,6,7,11bα-hexahydro-2H-benzo[a]quinolizine (2.16 g) and triethylamine (1.2 g) in dichloromethane (25 cm³) was treated with a solution of 3-chloropropanesulphonyl chloride (1.77 g,) in dichloromethane (25 cm³). The clear solution was kept at room temperature for 3 days, then washed with water (50 cm³), brine (50 cm³), and dried (MgSO₄). Filtration and evaporation gave an orange gum which was chromatographed on silica eluted with 10% ethanol-ethyl acetate to give a yellow gum (2.68 g). This was dissolved in ethanol (10 cm³), acidified with ethanolic HCl, and the crystals were collected by filtration, washed with 10% ethanol-ethyl acetate and dried at 80°/100 mm to give the title compound as the hydrochloride, (2.53 g), very pale cream plates, m.p. 253°–255° (dec).

I claim:

1. A compound selected from the group consisting of a benzoquinolizine of the formula

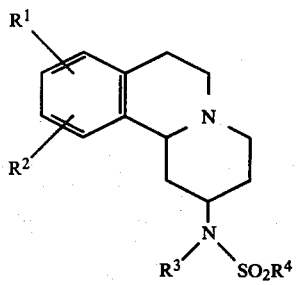

and a pharmaceutically acceptable acid addition salt thereof, wherein R¹ and R² each represent hydrogen, lower alkyl, lower alkoxy or halogen, R³ represents methyl or ethyl and R⁴ represents mono- poly-halo(lower)alkyl.

2. A compound according to claim 1 which is N-methyl-N-(1,3,4,6,7,11bα-hexahydro-2H-benzo[a]quinolizin-2β-yl)-trifluoromethanesulphonamide or a pharmaceutically acceptable acid addition salt thereof.

3. A compound according to claim 1 which is N-methyl-N-(1,3,4,6,7,11bα-hexahydro-2H-benzo[a]quinolizin-2β-yl)-2′,2′,2′-trifluoroethanesulphonamide or a pharmaceutically acceptable acid addition salt thereof.

4. A compound according to claim 1 which is N-methyl-N-(1,3,4,6,7,11bα-hexahydro-2H-benzo[a]quinolizin-2β-yl)chloromethanesulphonamide or a pharmaceutically acceptable acid addition salt thereof.

5. A compound according to claim 1 which is N-methyl-N-(1,3,4,6,7,11bα-hexahydro-2H-benzo[a]quinolizin-2β-yl)-3′-chloropropanesulphonamide or a pharmaceutically acceptable acid addition salt thereof.

6. A pharmaceutical composition having α₂-adrenoceptor antagonistic activity comprising an amount effective to antagonise α₂-adrenoceptors of a compound selected from the group consisting of a benqoquinolizine of the formula

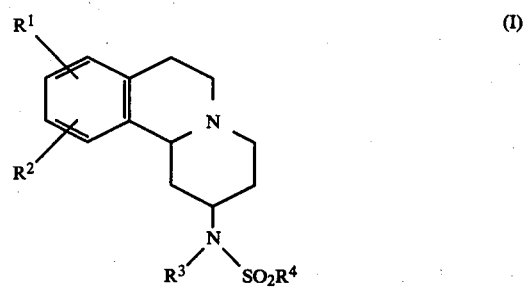

and a pharmaceutically acceptable acid addition salt thereof, wherein R¹ and R² each represent hydrogen, lower alkyl, lower alkoxy or halogen, R³ represents methyl or ethyl and R⁴ represents halo(lower)alkyl.

7. A method of antagonising α₂-adrenoceptors in warm blooded animals which comprises administering to the animal an effective amount of a compound selected from the group consisting of a benzoquinolizine of the formula

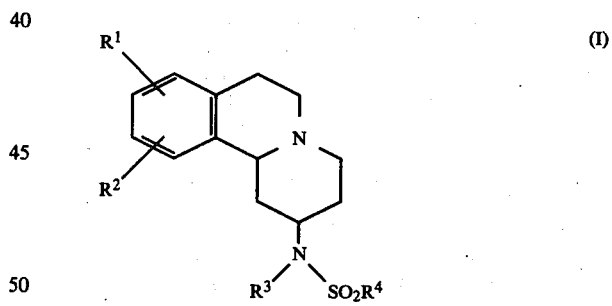

and a pharmaceutically acceptable acid addition salt thereof, wherein R¹ and R² each represent hydrogen, lower alkyl, lower alkoxy or halogen, R³ represents methyl or ethyl and R⁴ represents halo(lower)alkyl.

* * * * *